US009115218B2

(12) United States Patent
Charvet et al.

(10) Patent No.: US 9,115,218 B2
(45) Date of Patent: *Aug. 25, 2015

(54) ANIONIC POLYSACCHARIDES FUNCTIONALIZED BY AT LEAST TWO HYDROPHOBIC GROUPS CARRIED BY AN AT LEAST TRIVALENT SPACER

(75) Inventors: Richard Charvet, Rillieux la Pape (FR); Remi Soula, Lyons (FR); Olivier Soula, Meyzieu (FR)

(73) Assignee: ADOCIA, Lyons (FR)

( * ) Notice: Subject to any disclaimer, the term of this patent is extended or adjusted under 35 U.S.C. 154(b) by 759 days.

This patent is subject to a terminal disclaimer.

(21) Appl. No.: 13/024,100

(22) Filed: Feb. 9, 2011

(65) Prior Publication Data

US 2011/0195913 A1     Aug. 11, 2011

Related U.S. Application Data

(60) Provisional application No. 61/282,846, filed on Apr. 8, 2010, provisional application No. 61/302,823, filed on Feb. 9, 2010.

(30) Foreign Application Priority Data

Apr. 8, 2010 (FR) .................................. 10 01474
Nov. 19, 2010 (WO) .................. PCT/IB2010/002970

(51) Int. Cl.
*A61K 47/36* (2006.01)
*A61K 38/02* (2006.01)
*C08B 37/02* (2006.01)

(52) U.S. Cl.
CPC ............. *C08B 37/0021* (2013.01); *A61K 47/36* (2013.01); *A61K 38/02* (2013.01)

(58) Field of Classification Search
None
See application file for complete search history.

(56) References Cited

U.S. PATENT DOCUMENTS

| | | | |
|---|---|---|---|
| 2,387,201 | A | 10/1945 | Weiner |
| 4,455,256 | A | 6/1984 | Urist |
| 4,826,818 | A | 5/1989 | Mori et al. |
| 5,650,176 | A | 7/1997 | Lee et al. |
| 5,683,461 | A | 11/1997 | Lee et al. |
| 2004/0220143 | A1 | 11/2004 | Byun et al. |
| 2007/0015701 | A1 | 1/2007 | Zalipsky et al. |
| 2007/0142324 | A1* | 6/2007 | Perly et al. ...................... 514/58 |
| 2008/0014250 | A1 | 1/2008 | Soula et al. |
| 2008/0234227 | A1 | 9/2008 | Soula et al. |
| 2009/0048412 | A1 | 2/2009 | Soula et al. |
| 2009/0155320 | A1 | 6/2009 | Rudin et al. |
| 2009/0291114 | A1 | 11/2009 | Soula et al. |
| 2010/0009911 | A1 | 1/2010 | Soula |
| 2010/0137456 | A1 | 6/2010 | Soula et al. |
| 2010/0166867 | A1 | 7/2010 | Soula et al. |
| 2010/0167991 | A1 | 7/2010 | Soula et al. |

FOREIGN PATENT DOCUMENTS

| | | |
|---|---|---|
| EP | 1 891 984 A1 | 2/2008 |
| FR | 2 861 396 | 4/2005 |
| FR | 2 914 305 | 10/2008 |
| FR | 2 933 306 | 1/2010 |
| FR | 2 934 999 A1 | 2/2010 |
| WO | WO 2007/116143 A1 | 10/2007 |
| WO | WO 2009/016131 A1 | 2/2009 |
| WO | WO 2009/127940 A1 | 10/2009 |
| WO | WO 2009/144578 A2 | 12/2009 |
| WO | WO 2010/041119 A1 | 4/2010 |
| WO | WO 2010/058106 A1 | 5/2010 |

OTHER PUBLICATIONS

Patani, G. A. et al. (1996) Chem. Rev. 96; pp. 3147-3176.*
Office Action dated Dec. 20, 2012 issued in U.S. Appl. No. 12/950,616.
Written Opinion issued Jun. 5, 2012 in International Application No. PCT/IB2010/002970.
French Search Report dated Apr. 27, 2010 issued in French Patent Application No. FR 0903803 (with translation).
International Search Report mailed May 4, 2010 issued in International Patent Application No. PCT/FR2009/001332 (with translation).
Urist, "Bone: Formation by Autoinduction," Science (1965), vol. 150, pp. 893-899.
Scheufler et al., "Crystal Structure of Human Bone Morphogenetic Protein-2 at 2.7 A Resolution," J. Mol. Biol. (1999), vol. 287 pp. 103-115.
Schlunegger et al., "Refined Crystal Structure of Human Transforming Growth Factor β2 at 1 95 A Resolution," J. Mol. Biol. (1993), vol. 231, pp. 445-458.
Israel et al., "Heterodimeric Bone Morphogenetic Proteins Show Enhanced Activity In Vitro and In Vivo," Growth Factors (1996), vol. 13, pp. 291-300.
Chen et al., "Bone Morphogenetic Proteins," Growth Factors, Dec. 2004, vol. 22, pp. 233-241.
Cheng et al., "Osteogenic Activity of the Fourteen Types of Human Bone Morphogenetic Proteins (BMPs)," Bone and Joint Surgery (2003), pp. 1544-1552.
Seeherman et al., "Bone Morphogenetic Protein Delivery Systems," Spine, (2002), vol. 27, No. 16S, pp. S16-S23.
Bohner, "Calcium Orthophosphates in Medicine: From Ceramics to Calcium Phosphate Cements," Injury (2000), vol. 31, S-D37-S-D47.
Boden et al., "Use of Recombinant Human Bone Morphogenetic Protein-2 to Achieve Posterolateral Lumbar Spine Fusion in Humans," Spine, vol. 27, No. 23, pp. 2662-2673 (2002).
Kim et al., "Characterization of a Calcium Phosphate-Based Matrix for rhBMP-2," Methods in Molecular Biology (2004), vol. 238, pp. 49-64.

(Continued)

*Primary Examiner* — Kevin S Orwig
(74) *Attorney, Agent, or Firm* — Oliff PLC

(57) ABSTRACT

Anionic polysaccharide derivatives partially functionalized by at least two vicinal hydrophobic groups, the hydrophobic groups, which are identical or different, being carried by an at least trivalent radical or spacer, a method of synthesis of the functionalized polysaccharides, and pharmaceutical compositions having one of the polysaccharides and at least one active principle are provided.

22 Claims, No Drawings

(56) References Cited

OTHER PUBLICATIONS

Hoffman, "Hydrogels for Biomedical Applications," Adv. Drug Deliv. Rev. (2002), vol. 43, pp. 3-12.
Peppas et al., "Hydrogels in Pharmaceutical Formulations," Eur. J. Pharm. Biopharm. (2000), vol. 50, pp. 27-46.
Coviello et al., "Polysaccharide Hydrogels for Modified Release Formulations," J. Control. Release (2007), vol. 119, pp. 5-24.
Lawrence et al., "rhBMP-2 (ACS and CRM Formulations) Overcomes Pseudarthrosis in a New Zealand White Rabbit Posterolateral Fusion Model," Spine, vol. 32, No. 11, pp. 1206-1213 (2007).
Yao et al., "Evaluation of Insoluble Bone Gelatin as a Carrier for Enhancement of Osteogenetic Protein-I-Induced Intertransverse Process Lumbar Fusion in a Rabbit Model," Spine, vol. 33, No. 18, pp. 1935-1942 (2008).
Magit et al., "Healos/Recombinant Human Growth and Differentiation Factor-5 Induces Posterolateral Lumbar Fusion in a New Zealand White Rabbit Model," Spine, vol. 31, No. 19, pp. 2180-2188 (2006).
U.S. Appl. No. 61/129,023 in the name of Olivier Soula filed May 30, 2008.
U.S. Appl. No. 61/129,617 in the name of Olivier Soula filed Jul. 8, 2008.
U.S. Appl. No. 61/129,011 in the name of Gerard Soula filed May 30, 2008.
U.S. Appl. No. 61/129,618 in the name of Gerard Soula filed Jul. 8, 2008.
U.S. Appl. No. 61/129,616 in the name of Olivier Soula filed Jul. 8, 2008.
U.S. Appl. No. 61/129,012 in the name of Olivier Soula filed May 30, 2008.
U.S. Appl. No. 61/193,217 in the name of Olivier Soula filed Nov. 6, 2008.
U.S. Appl. No. 61/193,216 in the name of Olivier Soula filed Nov. 6, 2008.
Dohzono et al., "Successful Spinal Fusion by *E. Coli*-Derived BMP-2-adsorbed Porous β-TCP Granules," Clin. Orthop., Relat. Res., 2009, pp. 1-6.
Seeherman et al., "A Review of Preclinical Program Development for Evaluating for Evaluation Injectable Carriers for Osteogenic Factors," J. of Bone and Joint Surgery, 2003, vol. 85-A, Supp. 3, pp. 96-108.
Wang et al., "Controlled-Release of rhBMP-2 Carriers in the Regeneration of Osteonecrotic Bone," Biomaterials, 2009, vol. 30 pp. 4178-4186.
Dawson et al., "Recombinant Human Bone Morphogenetic Protein-2 on an Absorbable Collagen Sponge with an Osteoconductive Bulking Agent in Posterolateral Arthrodesis with Instrumentation," J. of Bone and Joint Surgery, 2009, pp. 1604-1613.
U.S. Appl. No. 12/461,326, filed Aug. 7, 2009 in the name of Remi Soula.
Chubinskaya, et al., "OP-1/BMP-7 in cartilage repair," International Orthopaedics (SICOT), 2007, vol. 31, pp. 773-781.
Zeisberg, et al., "Bone Morphogenic Protein-7 Induces Mesenchymal to Epithelial Transition in Adult Renal Fibroblasts and Facilitates Regeneration of Injured Kidney," The Journal of Biological Chemistry, vol. 280, No. 9, Issue of Mar. 4, 2005, pp. 8094-8100.
Sugimoto, et al., "BMP-7 Functions as a novel hormone to facilitate liver regeneration," The FASEB Journal, Research Communication, Jan. 2007, vol. 21, pp. 256-264.
Kinoshita, et al., "Adenovirus-medicated expression of BMP-7 suppresses the development of liver fibrosis in rats," Gut, 2007, vol. 56, pp. 706-714.
Gressner, et al., "Changing the pathogenetic roadmap of liver fibrosis? Where did it start; where will it go?," Journal of Gastroenterology and Hepatology, 2008, vol. 23, pp. 1024-1035.

Saika, et al., "Therapeutic effects of adenoviral gene transfer of bone morphogenic protein-7 on a corneal alkali injury model in mice," Laboratory Investigation (2005), vol. 85, pp. 474-486.
Chang, et al., "Intravenous Administration of Bone Morphogenetic Protein-7 After Ischemia Improves Motor Function in Stroke Rats," Stroke (2003), vol. 34, pp. 558-564.
Zeisberg, et al., "Endothelial-to-mesenchymal transition contributes of cardiac fibrosis," Nature Medicine, 2007, vol. 13,. No. 8, pp. 952-961.
Myllarniemi, et al., "Gremlin-mediated Decrease in Bone Morphogenetic Protein Signaling Promotes Pulmonary Fibrosis," American Journal of Respiratory and Critical Care Medicine, 2008, vol. 177, pp. 321-329.
De Rivero Vaccari, et al., "Neuroprotective effects of bone morphogenetic protein 7 (BMP7) treatment after spinal cord injury," Neuroscience Letters 465, 2009, pp. 226-229.
Harvey, et al., "Neurotrophic effects of bone morphogenetic protein-7 in a rat model of Parkinson's desease," Brain Research 1022, 2004, pp. 88-95.
Moreno-Miralles, et al., "New Insights into bon morphogenetic protein signaling: focus on angiogenesis," Current Opinion in Hematology, 2008, vol. 16, pp. 195-201.
David, et al., "Emerging role of bone morphogenetic proteins in angiogenesis," Cytokine & Growth Factor Review, 2009, vol. 20, pp. 203-212.
Hwang, et al., "Immunogenicity of osteogenic protein 1: results from a prospective, randomized, controlled, multicenter pivotal study of uninstrumented lumbar posterolateral fusion," J Neurosurg Spin, 2010, vol. 13, pp. 484-493.
Vukicevic, et al., "Systemic administration of bone morphogenetic proteins," Birkhauser Verlag Basel, 2008, pp. 317-337.
Swencki-Underwood, et al., "Expression and characterization of a human BMP-7 variant with improved biochemical properties," Protein Expression & Purification, 2008, vol. 57, pp. 312-319.
Sanchez-Chaves, et al., "Poly (vinyl alcohol) functionalized by monosuccinate groups. Coupling of bioactive amino compounds," Polymer, 1998, vol. 39, No. 13, pp. 2751-2757.
Paul, et al., "N,N[1]-Carbonyldiimidazole in Peptide Synthesis. III.[1] A synthesis of Isoleucine-5 Angiotensin II Amide-1," Organic Chemical, 1962, vol. 27, pp. 2094-2099.
Dale, et al., "The Process Development of a Scaleable Route to the PDE5 Inhibitor UK-357,903," Organic Process Research & Development, 2002, vol. 6, pp. 767-772.
Mire-Sluis, et al., "Recommendations for the design and optimization of immunoassays used in the detection of host antibodies against biotechnology products," Journal of Immunological Methods, 2004, vol. 289, pp. 1-16.
Hwang, et al., "Immunogenicity of Bone Morphogentic Proteins," J. Neurosurg Spine, 2009, vol. 10, pp. 443-451.
Knolker, et al., "Isocyanates, Part 4,[10] Convenient Phosgene-Free Method for the Synthesis and Derivatization of Enantiopure a-Isocyanato Carboxylic Acid Esters," Synlett, Aug. 1997, pp. 925-928.
French Search Report dated Oct. 1, 2010 issued in French Patent Application No. 737360.
U.S. Appl. No. 12/950,616 in the name of Reim Soula et al, filed Nov. 19, 2010.
U.S. Appl. No. 12/591,442 in the name of Olivier Soula, et al. filed Nov. 19, 2009.
Pal, et al., "Molecular mechanism of physical gelation of hydrocarbons by fatty acid amides of natural amino acids," Tetrahedron, 2007, vol. 63, pp. 7334-7348.
U.S. Office Action dated Jun. 26, 2013 from U.S. Appl. No. 12/950,616.

\* cited by examiner

ANIONIC POLYSACCHARIDES FUNCTIONALIZED BY AT LEAST TWO HYDROPHOBIC GROUPS CARRIED BY AN AT LEAST TRIVALENT SPACER

The present invention relates to novel biocompatible polymers based on anionic polysaccharides functionalized by at least two hydrophobic groups carried by an at least trivalent spacer, which polymers can be used in particular for the administration of active principle(s) (AP(s)) to man or animals with a therapeutic and/or prophylactic purpose.

Anionic polysaccharides functionalized by at least two vicinal hydrophobic groups are, as a result of their structure and their biocompatibility, particularly advantageous in the pharmaceutical field and more particularly in the field of the stabilization of protein active principles by the formation of complexes.

Molecular compounds, such as phospholipids and triglycerides, which carry at least two vicinal hydrophobic chains, that is to say chains joined by one and the same group, are known, in particular from the natural constituents of cell membranes. These compounds are very important, in particular for the stabilization of transmembrane proteins. However, they are molecules of low molar mass and of high hydrophobicity which dissolve only in complex structures, such as vesicles.

It is to the credit of the Applicant Company to have synthesized polysaccharides functionalized by radicals carrying two biocompatible vicinal hydrophobic chains. These polymeric compounds, the hydrophobicity of which can be adjusted, are of major advantage in the formulation of pharmaceutical active principles.

The present invention relates to novel anionic polysaccharides functionalized by at least two vicinal hydrophobic groups, said hydrophobic groups, which are identical or different, being carried by an at least trivalent radical or spacer. In one embodiment, the carboxyls of the polysaccharide are partially substituted by at least two hydrophobic radicals, said hydrophobic radicals, which are identical or different, being carried by an at least trivalent radical or spacer. In one embodiment, the hydroxyls of the polysaccharides are partially substituted by at least two hydrophobic radicals, said hydrophobic radicals, which are identical or different, being carried by an at least trivalent radical or spacer. These novel anionic polysaccharides comprising hydrophobic groups have a good biocompatibility and their hydrophobicity can be easily adjusted without detrimentally affecting the biocompatibility and the stability.

It also relates to their methods of synthesis.

In one embodiment, the polysaccharide is chosen from polysaccharides comprising carboxyls, said polysaccharides being chosen either from polysaccharides which naturally carry carboxyls or being chosen from synthetic polysaccharides obtained from polysaccharides naturally comprising carboxyls or obtained from neutral polysaccharides, hydroxyls of which have been converted to carboxyls, and chosen from polysaccharides, at least one of the carboxyls or at least one of the hydroxyls of which is substituted by at least two hydrophobic radicals, denoted -Hy, which are identical or different:

said hydrophobic radicals (-Hy) being grafted or bonded to the anionic polysaccharide by a connecting arm R, said connecting arm R carrying at least three reactive functional groups and being bonded to the polysaccharide by a bond F resulting from the coupling between a reactive functional group of the precursor of the connecting arm R' and a carboxyl or a hydroxyl of the anionic polysaccharide and said hydrophobic radicals (-Hy) being bonded to the connecting arm R by at least one functional group G resulting from the coupling between a reactive functional group of a hydrophobic compound (Hy') and a reactive functional group of the precursor of the connecting arm R', the nonfunctionalized carboxyls of the anionic polysaccharide being in the cationic carboxylate form, the cation preferably being that of an alkali metal, such as $Na^+$ or $K^+$, F being either an amide, ester or carbamate functional group, G being either an amide, ester or carbamate functional group, Hy being a radical, resulting from the coupling between a reactive functional group of a hydrophobic compound (Hy') and a reactive functional group of the precursor of the connecting arm R', composed of a chain comprising from 4 to 50 carbon atoms which is optionally branched and/or unsaturated, which optionally comprises one or more heteroatoms, such as O, N and/or S, and which optionally comprises one or more saturated, unsaturated or aromatic rings or heterocycles, R being a trivalent radical, composed of a chain comprising from 1 to 15 carbon atoms which is optionally branched and/or unsaturated, which optionally comprises one or more heteroatoms, such as O, N and/or S, and which optionally comprises one or more saturated, unsaturated or aromatic rings or heterocycles, resulting from the reaction of a precursor R' having at least three reactive functional groups, which are identical or different, chosen from the group consisting of the alcohol, acid and amine functional groups.

The invention thus relates to anionic polysaccharides chosen from polysaccharides comprising carboxyls, said polysaccharides being chosen either from polysaccharides which naturally carry carboxyls or being chosen from synthetic polysaccharides obtained from polysaccharides naturally comprising carboxyls or obtained from neutral polysaccharides, hydroxyls of which have been converted to carboxyls, and chosen from polysaccharides, at least one of the hydroxyls of which is substituted by at least two hydrophobic radicals, denoted $-Hy_h$, or at least one of the carboxyls of which is substituted by at least two hydrophobic radicals, denoted $-Hy_c$, which are identical or different, of formula I:

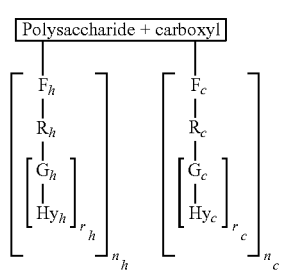

Formula I

In which $n_c$ and $n_h$ represent the degree of functionalization of the saccharide units of the polysaccharide by $—F_c—R_c\text{-}[G_c\text{-}Hy_c]_{rc}$ and/or $—F_h—R_h\text{-}[G_h\text{-}Hy_h]_{rh}$ and $n_h \geq 0$ and $n_c \geq 0$ with $0.01 \leq n_h + n_c \leq 0.5$, $F_c$ being either an amide functional group or an ester functional group, $F_h$ being a carbamate functional group, the nonfunctionalized carboxyls of the anionic polysaccharide being in the cation carboxylate form, the cation preferably being that of an alkali metal, such as $Na^+$ or $K^+$, $G_h$ or $G_c$ being either an amide functional group or an ester functional group or a carbamate functional group resulting from the coupling between a reactive functional group of a hydrophobic compound ($Hy_h'$ or $Hy_c'$) and a reactive functional group of the precursor of the connecting arm $R_h'$ or $R_c'$, $Hy_h$ or $Hy_c$ being radicals, which are identical or different, resulting from the coupling between a reactive functional group of a hydrophobic compound ($Hy_h'$ or $Hy_c'$) and a reactive functional group of the precursor of the connecting arm $R_h'$ or $R_c'$, $Hy_h$ or $Hy_c$ being composed of a chain comprising from 4 to 50 carbons which is optionally branched and/or unsaturated, which optionally comprises one or more heteroatoms, such as O, N and/or S, and which optionally comprises one or more saturated, unsaturated or aromatic rings or heterocycles, $R_c$ being a trivalent radical, composed of a chain comprising from 1 to 15 carbons which is optionally branched and/or unsaturated, which optionally comprises one or more heteroatoms, such as O, N and/or S, and which optionally comprises one or more saturated, unsaturated or aromatic rings or heterocycles, resulting from the reaction of a precursor $R_c'$ having at least three reactive functional groups, which are identical or different, chosen from the group consisting of the alcohol, acid and amine functional groups, $R_h$ being a trivalent radical, composed of a chain comprising from 1 to 15 carbons which is optionally branched and/or unsaturated, which optionally comprises one or more heteroatoms, such as O, N and/or S, and which optionally comprises one or more saturated, unsaturated or aromatic rings or heterocycles, resulting from the reaction of a precursor $R_h'$ having at least three reactive functional groups, one being an amine and the others being chosen from the group consisting of the alcohol, acid and amine functional groups, $r_h$ being an integer representing the number of hydrophobic groups grafted to the at least trivalent connecting arm $R_h$ and $2 \leq r_h \leq 4$, $r_c$ being an integer representing the number of hydrophobic groups grafted to the at least trivalent connecting arm $R_c$ and $2 \leq r_c \leq 4$.

In one embodiment, $n_h + n_c$ is from 0.02 to 0.4.

In one embodiment, $n_h + n_c$ is from 0.03 to 0.3.

In one embodiment, the polysaccharide according to the invention is chosen from the group of the polysaccharides of formula II:

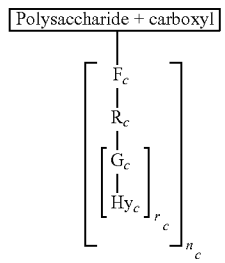

Formula II in which $n_c$ represents the degree of functionalization of the carboxyls of the polysaccharide by an $-F_c-R_c-[G_c-Hy_c]_{rc}$ sequence and is from 0.01 to 0.5, $F_c$, $R_c$, $G_c$, $Hy_c$ and $r_c$ correspond to the definitions given above, when the carboxyls of the polysaccharide are not functionalized by $-F_c-R_c-[G_c-Hy_c]_{rc}$, then the carboxyl or carboxyls of the polysaccharide are cation carboxylates, the cation preferably being that of an alkali metal, such as $Na^+$ or $K^+$, and, when a nonfunctionalized reactive functional group of the connecting arm $R_c$ is an acid functional group, it is also in the salified form, in the cation carboxylate form, the cation preferably being that of an alkali metal, such as $Na^+$ or $K^+$, and, when a nonfunctionalized reactive functional group of the connecting arm $R_c$ is an amine functional group, it is in the form of an anion salt, the anion preferably being that of a halide.

In one embodiment, the polysaccharide according to the invention is chosen from the group of the polysaccharides of formula III:

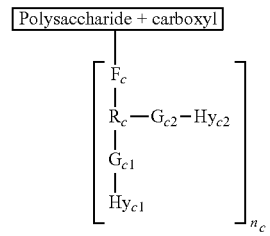

Formula III in which:

$n_c$, $F_c$ and $R_c$ correspond to the definitions given above, $G_{c1}$ and $G_{c2}$, which are identical or different, correspond to the definition of $G_c$, $Hy_{c1}$ and $Hy_{c2}$, which are identical or different, correspond to the definition of $Hy_c$.

In one embodiment, the polysaccharide according to the invention is chosen from the group of the polysaccharides of formula IV:

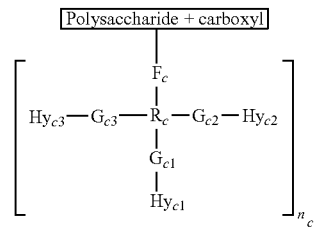

Formula IV in which:

$n_c$, $F_c$ and $R_c$ correspond to the definitions given above, $G_{c1}$, $G_{c2}$ and $G_{c3}$, which are identical or different, correspond to the definition of $G_c$, $Hy_{c1}$, $Hy_{c2}$ and $Hy_{c3}$, which are identical or different, correspond to the definition of $Hy_c$.

In one embodiment, the polysaccharide according to the invention is chosen from the group of the polysaccharides of formula V:

Formula V

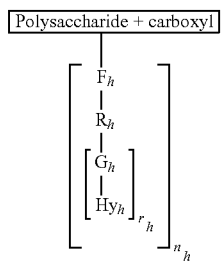

in which $n_h$ represents the degree of functionalization of the hydroxyls of the polysaccharide by an $—F_h—R_h-[G_h-Hy_h]_{r_h}$ sequence and is from 0.01 to 0.5, $F_h$, $R_h$, $G_h$, $Hy_h$ and $r_h$ correspond to the definitions given above, the carboxyls of the polysaccharide are in the cation carboxylate form, the cation preferably being that of an alkali metal, such as $Na^+$ or $K^+$, and, when a nonfunctionalized reactive functional group of the connecting arm $R_h$ is an acid functional group, it is also in the salified form, in the cation carboxylate form, the cation preferably being that of an alkali metal, such as $Na^+$ or $K^+$, and, when a nonfunctionalized reactive functional group of the connecting arm $R_h$ is an amine functional group, it is in the form of an anion salt, the anion preferably being that of a halide.

In one embodiment, the polysaccharide according to the invention is chosen from the group of the polysaccharides of formula VI:

Formula VI

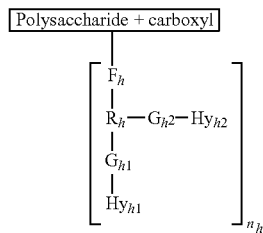

in which:
$n_h$, $F_h$ and $R_h$ correspond to the definitions given above,
$G_{h1}$ and $G_{h2}$, which are identical or different, correspond to the definition of $G_h$,
$Hy_{h1}$ and $Hy_{h2}$, which are identical or different, correspond to the definition of $Hy_h$.

In one embodiment, the polysaccharide according to the invention is chosen from the group of the polysaccharides of formula VII:

Formula VII

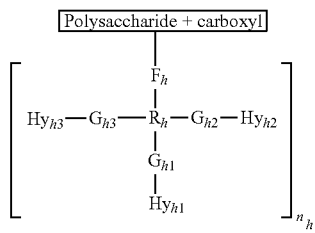

in which:
$n_h$, $F_h$ and $R_h$ correspond to the definitions given above,
$G_{h1}$, $G_{h2}$ and $G_{h3}$, which are identical or different, correspond to the definition of $G_h$,
$Hy_{h1}$, $Hy_{h2}$ and $Hy_{h3}$, which are identical or different, correspond to the definition of $Hy_h$.

The term "groups" or "derivatives" or "radicals", in particular Hy, R or Q, is understood to mean the mono- or polyvalent sequences resulting from the reactions between the precursors or between the precursors and the polysaccharides.

The precursors, such as Hy', R' and Q', are defined compounds which can, for example, be hydrophobic alcohols, hydrophobic amines, hydrophobic acids or amino acids which will react to give mono- or polyvalent groups or derivatives or radicals Hy, R and Q as defined above.

The term "anionic" is understood to mean a polysaccharide which comprises nonfunctionalized and salifiable carboxyls.

The term "degree of functionalization" is understood to mean the number of $—F_c—R_c-[G_c-Hy_c]_{r_c}$ and/or $—F_h—R_h-[G_h-Hy_h]_{r_h}$ groups per saccharide unit or, in other words, the total number of $—F_c—R_c-[G_c-Hy_c]_{r_c}$ and/or $—F_h—R_h-[G_h-Hy_h]_{r_h}$ groups with respect to the total number of saccharide units. This notion can also be expressed as molar fraction of the hydroxyls or carboxyls of the polysaccharide which are functionalized by $—F_c—R_c-[G_c-Hy_c]_{r_c}$ and/or $—F_h—R_h-[G_h-Hy_h]_{r_h}$.

The term "degree of conversion" is understood to mean the number of hydroxyls converted to carboxyls per saccharide unit or, in other words, the total number of hydroxyls converted to carboxyls with respect to the total number of saccharide units. This notion can also be expressed as molar fraction. For example, polysaccharides for which the degree of conversion of hydroxyls to carboxyls per saccharide unit is equal to or greater than 0.15 are polysaccharides for which at least 15 carboxyls per 100 saccharide units have been grafted.

The term "degree of polymerization m" is understood to mean the mean number of repeated units (monomers) per polymer chain. It is calculated by dividing the number-average molar mass by the average weight of the repeat unit.

The term "number-average molar mass ($M_n$)" is understood to mean the arithmetic mean of the weights of each of the polymer chains. Thus, for a number $n_i$ of chains i of molar mass $M_i$, $M_n=(\Sigma_i n_i M_i)/(\Sigma_i n_i)$.

The weight-average molar mass ($M_w$) is obtained by $M_w=(\Sigma_i n_i M_i^2)/(\Sigma_i n_i M_i)$, $n_i$ being the number of polymer chains i of molar mass $M_i$.

The polymers can also be characterized by the distribution of chain lengths, also known as polydispersity index (PI), which is equal to $M_w$ divided by $M_n$.

In one embodiment, the polysaccharides comprising carboxyls are polysaccharides which naturally carry carboxyls and are chosen from the group consisting of alginate, hyaluronan and galacturonan.

In one embodiment, the polysaccharides comprising carboxyls are synthetic polysaccharides obtained from polysaccharides naturally comprising carboxyls or from neutral polysaccharides, for which the degree of conversion of the hydroxyls to carboxyls per saccharide unit is equal to or greater than 0.15, of general formula VIII:

Formula VIII

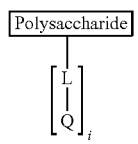

in which the natural polysaccharides are chosen from the group of the polysaccharides predominantly composed of monomers bonded via glycoside bonds of (1,6) and/or (1,4) and/or (1,3) and/or (1,2) type, L is a bond resulting from the coupling between a precursor of the connecting arm Q and an —OH functional group of the polysaccharide and is either an ester, carbamate or ether functional group, i represents the degree of conversion of the hydroxyls to L-Q sequences per saccharide unit of the polysaccharide, Q is chosen from the radicals of general formula IX:

Formula IX

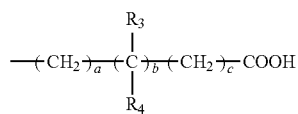

in which:
$1 \le a+b+c \le 6$, $0 \le a \le 3$, $0 \le b \le 3$, and $0 \le c \le 3$, $R_3$ and $R_4$, which are identical or different, are chosen from the group consisting of —H, linear or branched $C_1$ to $C_3$ alkyl, —COOH and the radical of general Formula X

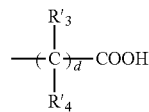

in which:
$1 \le d \le 3$ and $R'_3$ and $R'_4$, which are identical or different, are chosen from the group consisting of —H and a linear or branched $C_1$ to $C_3$ alkyl group.

In one embodiment, $a+b+c \le 5$.
In one embodiment, $a+b+c \le 4$.
In one embodiment, i is from 0.1 to 3.
In one embodiment, i is from 0.2 to 2.5.
In one embodiment, i is from 0.5 to 1.7.
In one embodiment, i is from 0.8 to 1.2.
In one embodiment, the polysaccharide is predominantly composed of monomers bonded via glycoside bonds of (1,6) type.
In one embodiment, the polysaccharide predominantly composed of monomers bonded via glycoside bonds of (1,6) type is dextran.
In one embodiment, the polysaccharide is predominantly composed of monomers bonded via glycoside bonds of (1,4) type.
In one embodiment, the polysaccharide predominantly composed of monomers bonded via glycoside bonds of (1,4) type is chosen from the group consisting of pullulan, alginate, hyaluronan, xylan, galacturonan and a water-soluble cellulose.

In one embodiment, the polysaccharide is a pullulan.
In one embodiment, the polysaccharide is an alginate.
In one embodiment, the polysaccharide is a hyaluronan.
In one embodiment, the polysaccharide is a xylan.
In one embodiment, the polysaccharide is a galacturonan.
In one embodiment, the polysaccharide is a water-soluble cellulose.
In one embodiment, the polysaccharide is predominantly composed of monomers bonded via glycoside bonds of (1,3) type.
In one embodiment, the polysaccharide predominantly composed of monomers bonded via glycoside bonds of (1,3) type is a curdlan.
In one embodiment, the polysaccharide is predominantly composed of monomers bonded via glycoside bonds of (1,2) type.
In one embodiment, the polysaccharide predominantly composed of monomers bonded via glycoside bonds of (1,2) type is an inulin.
In one embodiment, the polysaccharide is predominantly composed of monomers bonded via glycoside bonds of (1,4) and (1,3) type.
In one embodiment, the polysaccharide predominantly composed of monomers bonded via glycoside bonds of (1,4) and (1,3) type is a glucan.
In one embodiment, the polysaccharide is predominantly composed of monomers bonded via glycoside bonds of (1,4) and (1,3) and (1,2) type.
In one embodiment, the polysaccharide predominantly composed of monomers bonded via glycoside bonds of (1,4) and (1,3) and (1,2) type is mannan.
In one embodiment, the L-Q sequence of the polysaccharide according to the invention is chosen from the group consisting of the following sequences, L having the meaning given above:

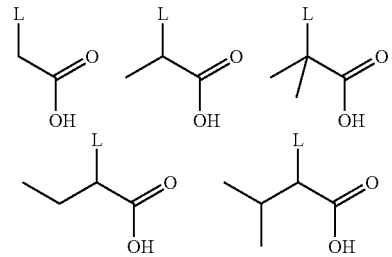

In one embodiment, the L-Q sequence of the polysaccharide according to the invention is chosen from the group consisting of the following sequences, L having the meaning given above:

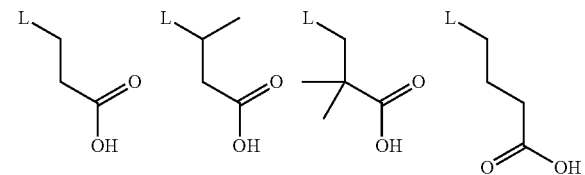

In one embodiment, the L-Q sequence of the polysaccharide according to the invention is chosen from the group consisting of the following sequences, L having the meaning given above:

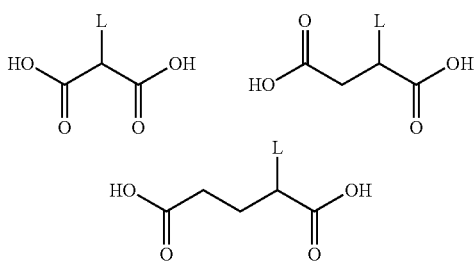

In one embodiment, the L-Q sequence of the polysaccharide according to the invention is the following sequence, L having the meaning above:

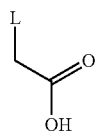

In one embodiment, the L-Q sequence of the polysaccharide according to the invention is the following sequence, L having the meaning above:

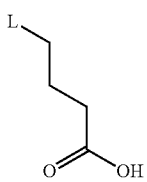

In one embodiment, the polysaccharides are chosen from the polysaccharides of formulae II, III and IV in which the -$Hy_c$ radical is a radical originating from a hydrophobic alcohol resulting from the coupling between the hydroxyl functional group of the hydrophobic alcohol and at least one reactive functional group carried by the precursor $R_c'$ of the at least trivalent radical $R_c$, and $G_c$ is either an ester functional group or a carbamate functional group, $R_c$ and $F_c$ having the definitions given above.

In one embodiment, the polysaccharides are chosen from the polysaccharides of formulae V, VI and VII in which the -$Hy_h$ radical is a radical originating from a hydrophobic alcohol resulting from the coupling between the hydroxyl functional group of the hydrophobic alcohol and at least one reactive functional group carried by the precursor $R_h'$ of the at least trivalent radical $R_h$, and $G_h$ is either an ester functional group or a carbamate functional group, $R_h$ and $F_h$ having the definitions given above.

In one embodiment, the hydrophobic alcohol is chosen from fatty alcohols.

In one embodiment, the hydrophobic alcohol is chosen from alcohols composed of a saturated or unsaturated and branched or unbranched alkyl chain comprising from 4 to 18 carbons.

In one embodiment, the hydrophobic alcohol is chosen from alcohols composed of a saturated or unsaturated and branched or unbranched alkyl chain comprising more than 18 carbons.

In one embodiment, the hydrophobic alcohol is octanol.

In one embodiment, the hydrophobic alcohol is dodecanol.

In one embodiment, the hydrophobic alcohol is 2-ethylbutanol.

In one embodiment, the hydrophobic alcohol is chosen from myristyl alcohol, cetyl alcohol, stearyl alcohol, cetearyl alcohol, butyl alcohol, oleyl alcohol or lanolin alcohol.

In one embodiment, the hydrophobic alcohol is chosen from cholesterol derivatives.

In one embodiment, the cholesterol derivative is cholesterol.

In one embodiment, the hydrophobic alcohol is chosen from menthol derivatives.

In one embodiment, the hydrophobic alcohol is menthol in its racemic form.

In one embodiment, the hydrophobic alcohol is the D isomer of menthol.

In one embodiment, the hydrophobic alcohol is the L isomer of menthol.

In one embodiment, the hydrophobic alcohol is chosen from tocopherols.

In one embodiment, the tocopherol is α-tocopherol.

In one embodiment, the α-tocopherol is the racemate of α-tocopherol.

In one embodiment, the tocopherol is the D isomer of α-tocopherol.

In one embodiment, the tocopherol is the L isomer of α-tocopherol.

In one embodiment, the hydrophobic alcohol is chosen from the alcohols carrying an aryl group.

In one embodiment, the alcohol carrying an aryl group is chosen from benzyl alcohol or phenethyl alcohol.

In one embodiment, the hydrophobic alcohol is chosen from unsaturated fatty alcohols.

In one embodiment, the unsaturated fatty alcohols are chosen from the group consisting of geraniol, β-citronellol and farnesol.

In one embodiment, the hydrophobic alcohol is 3,7-dimethyl-1-octanol.

In one embodiment, the polysaccharides are chosen from the polysaccharides of formulae II, III and IV in which the -$Hy_c$ radical is a radical originating from a hydrophobic acid resulting from the coupling between the carboxyl functional group of the hydrophobic acid and at least one reactive functional group carried by the precursor $R_c'$ of the at least trivalent radical $R_c$, and $G_c$ is either an ester functional group or an amide functional group, $R_c$ and $F_c$ having the definitions given above.

In one embodiment, the polysaccharides are chosen from the polysaccharides of formulae V, VI and VII in which the -$Hy_h$ radical is a radical originating from a hydrophobic acid resulting from the coupling between the carboxyl functional group of the hydrophobic acid and at least one reactive functional group carried by the precursor $R_h'$ of the at least trivalent radical $R_h$, and $G_h$ is either an ester functional group or an amide functional group, $R_h$ and $F_h$ having the definitions given above.

In one embodiment, the hydrophobic acid is chosen from fatty acids.

In one embodiment, the fatty acids are chosen from the group consisting of the acids composed of a saturated or unsaturated and branched or unbranched alkyl chain comprising from 6 to 50 carbons.

In one embodiment, the fatty acids are chosen from the group consisting of linear fatty acids.

In one embodiment, the linear fatty acids are chosen from the group consisting of caproic acid, enanthic acid, caprylic acid, capric acid, nonanoic acid, decanoic acid, undecanoic acid, dodecanoic acid, palmitic acid, stearic acid, arachidic acid, behenic acid, tricosanoic acid, lignoceric acid, heptacosanoic acid, octacosanoic acid and melissic acid.

In one embodiment, the fatty acids are chosen from the group consisting of unsaturated fatty acids.

In one embodiment, the unsaturated fatty acids are chosen from the group consisting of myristoleic acid, palmitoleic acid, oleic acid, elaidic acid, linoleic acid, α-linoleic acid, arachidonic acid, eicosapentaenoic acid, erucic acid and docosahexaenoic acid.

In one embodiment, the fatty acids are chosen from the group consisting of bile acids and their derivatives.

In one embodiment, the bile acids and their derivatives are chosen from the group consisting of cholic acid, dehydrocholic acid, deoxycholic acid and chenodeoxycholic acid.

In one embodiment, the fatty acids are chosen from the acids carrying an aryl group.

In one embodiment, the fatty acid carrying an aryl group is phenylacetic acid.

In one embodiment, the polysaccharides are chosen from the polysaccharides of formulae II, III and IV in which the -$Hy_c$ radical is a radical originating from a hydrophobic amine resulting from the coupling between the amine functional group of the hydrophobic amine and at least one reactive functional group carried by the precursor of the at least trivalent radical $R_c$, and $G_c$ is either an amide functional group or a carbamate functional group, $R_c$ and $F_c$ having the definitions given above.

In one embodiment, the polysaccharides are chosen from the polysaccharides of formulae V, VI and VII in which the -$Hy_h$ radical is a radical originating from a hydrophobic amine resulting from the coupling between the amine functional group of the hydrophobic amine and at least one reactive functional group carried by the precursor $R_h'$ of the at least trivalent radical $R_h$, and $G_h$ is either an amide functional group or a carbamate functional group, $R_h$ and $F_h$ having the definitions given above.

In one embodiment, the hydrophobic amine is chosen from fatty amines.

In one embodiment, the hydrophobic amine is chosen from the amines composed of a saturated or unsaturated and linear or branched alkyl chain comprising from 6 to 18 carbons.

In one embodiment, the fatty amine is dodecylamine.

In one embodiment, the fatty amine is chosen from myristylamine, cetylamine, stearylamine, cetearylamine, butylamine or oleylamine.

In one embodiment, the hydrophobic amine is chosen from the amines carrying an aryl group.

In one embodiment, the amine carrying an aryl group is chosen from benzylamine or phenethylamine.

The precursors described below are categorized according to the nature of their reactive functional groups; the latter are at least three in number but some of the precursors described below can comprise four or more reactive functional groups.

In one embodiment, the at least trivalent precursors $R_c'$ and $R_h'$ are chosen from amino acids carrying two acid functional groups.

The amino acids carrying two acid functional groups are chosen from the group consisting of aspartic acid, glutamic acid, methylaspartic acid, γ-carboxyglutamic acid, 2-aminopimelic acid, 2-aminoadipic acid and O-succinylhomoserine.

In one embodiment, the at least trivalent precursors $R_c'$ and $R_h'$ are aspartic acids.

In one embodiment, the at least trivalent precursors $R_c'$ and $R_h'$ are chosen from amino acids carrying two amine functional groups.

The amino acids carrying two amine functional groups are chosen from the group consisting of lysine, 5-hydroxylysine, 2,4-diaminobutyric acid, 2,3-diaminopropionic acid, ornithine and p-aminophenylalanine.

In one embodiment, the at least trivalent precursors $R_c'$ and $R_h'$ are lysines.

In one embodiment, the at least trivalent precursors $R_c'$ and $R_h'$ are chosen from amino acids carrying an alcohol functional group.

The amino acids carrying an alcohol functional group are chosen from the group consisting of serine, threonine, tyrosine, homoserine and α-methylserine.

In one embodiment, the at least trivalent precursors $R_c'$ and $R_h'$ are serines.

In one embodiment, the at least trivalent precursors $R_c'$ and $R_h'$ are chosen from alcohol amines.

The alcohol amines are chosen from the group consisting of tromethamine (Tris), 3-amino-1,2-propanediol, triethanolamine, hydroxymethyltyrosine, tyrosinol, serinol (2-amino-1,3-propanediol) and threoninol.

In one embodiment, the at least trivalent precursors $R_c'$ and $R_h'$ are either tromethamines or 3-amino-1,2-propanediols.

In one embodiment, the at least trivalent precursor $R_c'$ is chosen from diacid alcohols.

In one embodiment, the diacid alcohols are chosen from the group consisting of 3-hydroxy-3-methylglutaric acid, malic acid and N-(2-hydroxyethyl)iminodiacetic acid.

In one embodiment, the at least trivalent precursor $R_c'$ is chosen from dialcohol acids.

In one embodiment, the dialcohol acids are chosen from the group consisting of bicine, 2,2-bis(hydroxymethyl)propionic acid, 2,4-dihydroxycinnamic acid, 3,4-dihydroxyhydrocinnamic acid and 4,4-bis(4-hydroxyphenyl)valeric acid.

In one embodiment, the at least trivalent precursors $R_c'$ and $R_h'$ are chosen from triamines.

In one embodiment, the triamines are chosen from the group consisting of 2-(aminomethyl)-2-methyl-1,3-propanediamine and tris(2-aminoethyl)amine.

In one embodiment, the triamines are obtained by reaction between a diacid amine and two diamines in order to result in the formation of a triamine comprising two amide functional groups.

The diacid amines are chosen from the group consisting of aspartic acid, glutamic acid, methylaspartic acid, γ-carboxyglutamic acid, 2-aminopimelic acid, 2-aminoadipic acid and O-succinylhomoserine.

In one embodiment, the diacid amine is aspartic acid.

In one embodiment, the diamines are chosen from the group consisting of ethylenediamine and decarboxylated lysine and its derivatives.

In one embodiment, the diamines are chosen from the group consisting of diethylene glycol diamine and triethylene glycol diamine.

In one embodiment, the triamine is di(2-aminoethyl)aspartamide.

In one embodiment, the at least trivalent precursor $R_c'$ is chosen from triacid alcohols.

In one embodiment, the triacid alcohols are chosen from the group consisting of citric acid.

In one embodiment, the at least trivalent precursor $R_c'$ is chosen from trialcohols.

In one embodiment, the trialcohols are chosen from the group consisting of 2-hydroxymethyl-1,3-propanediol, phloroglucinol and 1,1,1-tris(hydroxymethyl)-propane.

In one embodiment, the at least trivalent precursor $R_c'$ is chosen from trialcohol acids.

In one embodiment, the trialcohol acids are chosen from the group consisting of aleuritic acid.

In one embodiment, the at least trivalent precursor $R_c'$ is chosen from polyols.

In one embodiment, the polyols are chosen from the group consisting of glycerol, diglycerol, triglycerol, pentaerythritol and $\alpha,\alpha'$-diglycerol.

In one embodiment, the polysaccharides according to the invention carry two -$Hy_{c1}$ and -$Hy_{c2}$ or -$Hy_{h1}$ and -$Hy_{h2}$ groups which are identical or different but which have the same reactive functional group and the $G_{c1}$ and $G_{c2}$ or $G_{h1}$ and $G_{h2}$ bonds are identical.

The following combinations are produced by way of examples.

In one embodiment, $F_c$ is an ester functional group, $G_{c1}$ and $G_{c2}$ are ester functional groups, $R_c'$ is a diacid alcohol and $Hy_{c1}$ and $Hy_{c2}$ are groups originating from a hydrophobic alcohol.

In one embodiment, $F_c$ is an ester functional group, $G_{c1}$ and $G_{c2}$ are ester functional groups, $R_c'$ is a trialcohol and $Hy_{c1}$ and $Hy_{c2}$ are groups originating from a hydrophobic acid.

In one embodiment, $F_c$ is an ester functional group, $G_{c1}$ and $G_{c2}$ are amide functional groups, is an alcohol diamine and $Hy_{c1}$ and $Hy_{c2}$ are groups originating from a hydrophobic acid.

In one embodiment, $F_c$ is an ester functional group, $G_{c1}$ and $G_{c2}$ are carbamate functional groups, is an alcohol diamine and $Hy_{c1}$ and $Hy_{c2}$ are groups originating from a hydrophobic alcohol.

In one embodiment, $F_c$ is an ester functional group, $G_{c1}$ and $G_{c2}$ are amide functional groups, $R_c'$ is an alcohol diacid and $Hy_{c1}$ and $Hy_{c2}$ are groups originating from a hydrophobic amine.

In one embodiment, $F_c$ is an ester functional group, $G_{c1}$ and $G_{c2}$ are carbamate functional groups, $R_c'$ is a trialcohol and $Hy_{c1}$ and $Hy_{c2}$ are groups originating from a hydrophobic amine.

In one embodiment, $F_c$ is an amide functional group, $G_{c1}$ and $G_{c2}$ are ester functional groups, $R_c'$ is a diacid amine and $Hy_{c1}$ and $Hy_{c2}$ are groups originating from a hydrophobic alcohol.

In one embodiment, $F_c$ is an amide functional group, $G_{c1}$ and $G_{c2}$ are ester functional groups, $R_c'$ is a dialcohol amine and $Hy_{c1}$ and $Hy_{c2}$ are groups originating from a hydrophobic acid.

In one embodiment, $F_c$ is an amide functional group, $G_{c1}$ and $G_{c2}$ are amide functional groups, is a triamine and $Hy_{c1}$ and $Hy_{c2}$ are groups originating from a hydrophobic acid.

In one embodiment, $F_c$ is an amide functional group, $G_{c1}$ and $G_{c2}$ are amide functional groups, $R_c'$ is a diacid amine and $Hy_{c1}$ and $Hy_{c2}$ are groups originating from a hydrophobic amine.

In one embodiment, $F_c$ is an amide functional group, $G_{c1}$ and $G_{c2}$ are carbamate functional groups, is a dialcohol amine and $Hy_{c1}$ and $Hy_{c2}$ are groups originating from a hydrophobic amine.

In one embodiment, $F_c$ is an amide functional group, $G_{c1}$ and $G_{c2}$ are carbamate functional groups, is a triamine and $Hy_{c1}$ and $Hy_{c2}$ are groups originating from a hydrophobic alcohol.

In one embodiment, $F_h$ is a carbamate functional group, $G_{h1}$ and $G_{h2}$ are ester functional groups, $R_h'$ is a diacid amine and $Hy_{h1}$ and $Hy_{h2}$ are groups originating from a hydrophobic alcohol.

In one embodiment, $F_h$ is a carbamate functional group, $G_{h1}$ and $G_{h2}$ are ester functional groups, $R_h'$ is a dialcohol amine and $Hy_{h1}$ and $Hy_{h2}$ are groups originating from a hydrophobic acid.

In one embodiment, $F_h$ is a carbamate functional group, $G_{h1}$ and $G_{h2}$ are amide functional groups, $R_h'$ is a triamine and $Hy_{h1}$ and $Hy_{h2}$ are groups originating from a hydrophobic acid.

In one embodiment, $F_h$ is a carbamate functional group, $G_{h1}$ and $G_{h2}$ are carbamate functional groups, $R_h'$ is a triamine and $Hy_{h1}$ and $Hy_{h2}$ are groups originating from a hydrophobic alcohol.

In one embodiment, $F_h$ is a carbamate functional group, $G_{h1}$ and $G_{h2}$ are amide functional groups, $R_h'$ is a diacid amine and $Hy_{h1}$ and $Hy_{h2}$ are groups originating from a hydrophobic amine.

In one embodiment, $F_h$ is a carbamate functional group, $G_{h1}$ and $G_{h2}$ are carbamate functional groups, $R_h'$ is a dialcohol amine and $Hy_{h1}$ and $Hy_{h2}$ are groups originating from a hydrophobic amine.

In one embodiment, the polysaccharides according to the invention carry two different $Hy_{c1}$ and $Hy_{c2}$ or $Hy_{h1}$ and $Hy_{h2}$ groups but the $G_{c1}$ and $G_{c2}$ or $G_{h1}$ and $G_{h2}$ bonds are identical.

The following combinations are produced by way of examples.

In one embodiment, $F_c$ is an ester functional group, $G_{c1}$ and $G_{c2}$ are ester functional groups, is a dialcohol acid and $Hy_{c1}$ is a radical originating from a hydrophobic alcohol and $Hy_{c2}$ is a radical originating from a hydrophobic acid.

In one embodiment, $F_c$ is an ester functional group, $G_{c1}$ and $G_{c2}$ are amide functional groups, $R_c'$ is an acid alcohol amine and $Hy_{c1}$ is a radical originating from a hydrophobic acid and $Hy_{c2}$ is a radical originating from a hydrophobic amine.

In one embodiment, $F_c$ is an amide functional group, $G_{c1}$ and $G_{c2}$ are ester functional groups, $R_c'$ is an acid alcohol amine and $Hy_{c1}$ is a radical originating from a hydrophobic alcohol and $Hy_{c2}$ is a radical originating from a hydrophobic acid.

In one embodiment, $F_c$ is an amide functional group, $G_{c1}$ and $G_{c2}$ are amide functional groups, $R_c'$ is a diamine acid and $Hy_{c1}$ is a radical originating from a hydrophobic acid and $Hy_{c2}$ is a radical originating from a hydrophobic amine.

In one embodiment, $F_h$ is a carbamate functional group, $G_{h1}$ and $G_{h2}$ are ester functional groups, $R_h'$ is an acid alcohol amine and $Hy_{h1}$ is a radical originating from a hydrophobic alcohol and $Hy_{h2}$ is a radical originating from a hydrophobic acid.

In one embodiment, $F_h$ is a carbamate functional group, $G_{h1}$ and $G_{h2}$ are amide functional groups, $R_h'$ is a diacide amine and $Hy_{h1}$ is a radical originating from a hydrophobic acid and $Hy_{h2}$ is a radical originating from a hydrophobic amine.

In one embodiment, $F_h$ is a carbamate functional group, $G_{h1}$ and $G_{h2}$ are carbamate functional groups, $R_h'$ is a diamine alcohol and $Hy_{h1}$ is a radical originating from a hydrophobic alcohol and $Hy_{h2}$ is a radical originating from a hydrophobic amine.

In one embodiment, the polysaccharides according to the invention carry two $Hy_{c1}$ and $Hy_{c2}$ or $Hy_{h1}$ and $Hy_{h2}$ groups which are identical or different but which have the same reactive functional group and the $G_{c1}$ and $G_{c2}$ or $G_{h1}$ and $G_{h2}$ bonds are different.

The following combinations are produced by way of examples.

In one embodiment, $F_c$ is an ester functional group, $G_{c1}$ is an ester functional group, $R_c'$ is a dialcohol amine, $G_{c2}$ is an amide functional group and $Hy_{c1}$ and $Hy_{c2}$ are groups originating from a hydrophobic acid.

In one embodiment, $F_c$ is an ester functional group, $G_{c1}$ is an ester functional group, $R_c'$ is an alcohol acid amine, $G_{c2}$ is a carbamate functional group and $Hy_{c1}$ and $Hy_{c2}$ are groups originating from a hydrophobic alcohol.

In one embodiment, $F_c$ is an amide functional group, $G_{c1}$ is an ester functional group, $R_c'$ is a diamine alcohol, $G_{c2}$ is an amide functional group and $Hy_{c1}$ and $Hy_{c2}$ are groups originating from a hydrophobic acid.

In one embodiment, $F_c$ is an amide functional group, $G_{c1}$ is an ester functional group, $R_c'$ is a diamine acid, $G_{c2}$ is a carbamate functional group and $Hy_{c1}$ and $Hy_{c2}$ are groups originating from a hydrophobic alcohol.

In one embodiment, $F_c$ is an ester functional group, $G_{c1}$ is an amide functional group, $R_c'$ is a dialcohol acid, $G_{c2}$ is a carbamate functional group and $Hy_{c1}$ and $Hy_{c2}$ are groups originating from a hydrophobic amine.

In one embodiment, $F_h$ is a carbamate functional group, $G_{h1}$ is an ester functional group, $R_h'$ is a diamine alcohol, $G_{h2}$ is an amide functional group and $Hy_{h1}$ and $Hy_{h2}$ are groups originating from a hydrophobic acid.

In one embodiment, $F_h$ is a carbamate functional group, $G_{h1}$ is an ester functional group, $R_h'$ is a diamine acid, $G_{h2}$ is a carbamate functional group and $Hy_{h1}$ and $Hy_{h2}$ are groups originating from a hydrophobic alcohol.

In one embodiment, $F_h$ is a carbamate functional group, $G_{h1}$ is an amide functional group, $R_h'$ is an alcohol acid amine, $G_{h2}$ is a carbamate functional group and $Hy_{h1}$ and $Hy_{h2}$ are groups originating from a hydrophobic amine.

In one embodiment, the polysaccharides according to the invention carry two different $Hy_{c1}$ and $Hy_{c2}$ or $Hy_{h1}$ and $Hy_{h2}$ groups and the $G_{c1}$ and $G_{c2}$ or $G_{h1}$ and $G_{h2}$ bonds are different.

The following combinations are produced by way of examples.

In one embodiment, $F_c$ is an ester functional group, $G_{c1}$ is an ester functional group, $R_c'$ is a dialcohol amine and $Hy_{c1}$ is a radical originating from a hydrophobic acid, $G_{c2}$ is a carbamate functional group and $Hy_{c2}$ is a radical originating from a hydrophobic alcohol.

In one embodiment, $F_c$ is an ester functional group, $G_{c1}$ is an ester functional group, $R_c'$ is an acid alcohol amine and $Hy_{c1}$ is a radical originating from a hydrophobic alcohol, $G_{c2}$ is an amide functional group and $Hy_{c2}$ is a radical originating from a hydrophobic acid.

In one embodiment, $F_c$ is an ester functional group, $G_{c1}$ is an amide functional group, $R_c'$ is an alcohol diamine and $Hy_{c1}$ is a radical originating from a hydrophobic acid, $G_{c2}$ is a carbamate functional group and $Hy_{c2}$ is a radical originating from a hydrophobic alcohol.

In one embodiment, $F_c$ is an ester functional group, $G_{c1}$ is an ester functional group, $R_c'$ is an alcohol diacid and $Hy_{c1}$ is a radical originating from a hydrophobic alcohol, $G_{c2}$ is an amide functional group and $Hy_{c2}$ is a radical originating from a hydrophobic amine.

In one embodiment, $F_c$ is an ester functional group, $G_{c1}$ is an ester functional group, $R_c'$ is a dialcohol acid and $Hy_{c1}$ is a radical originating from a hydrophobic acid, $G_{c2}$ is an amide functional group and $Hy_{c2}$ is a radical originating from a hydrophobic amine.

In one embodiment, $F_c$ is an ester functional group, $G_{c1}$ is an amide functional group, $R_c'$ is a dialcohol amine and $Hy_{c1}$ is a radical originating from a hydrophobic acid, $G_{c2}$ is a carbamate functional group and $Hy_{c2}$ is a radical originating from a hydrophobic amine.

In one embodiment, $F_c$ is an ester functional group, $G_{c1}$ is an ester functional group, $R_c'$ is a trialcohol and $Hy_{c1}$ is a radical originating from a hydrophobic acid, $G_{c2}$ is a carbamate functional group and $Hy_{c2}$ is a radical originating from a hydrophobic amine.

In one embodiment, $F_c$ is an ester functional group, $G_{c1}$ is an ester functional group, $R_c'$ is an acid dialcohol and $Hy_{c1}$ is a radical originating from a hydrophobic alcohol, $G_{c2}$ is a carbamate functional group and $Hy_{c2}$ is a radical originating from a hydrophobic amine.

In one embodiment, $F_c$ is an amide functional group, $G_{c1}$ is an ester functional group, $R_c'$ is a diamine acid and $Hy_{c1}$ is a radical originating from a hydrophobic alcohol, $G_{c2}$ is an amide functional group and $Hy_{c2}$ is a radical originating from a hydrophobic acid.

In one embodiment, $F_c$ is an amide functional group, $G_{c1}$ is an ester functional group, $R_c'$ is an alcohol diamine and $Hy_{c1}$ is a radical originating from a hydrophobic acid, $G_{c2}$ is a carbamate functional group and $Hy_{c2}$ is a radical originating from a hydrophobic alcohol.

In one embodiment, $F_c$ is an amide functional group, $G_{c1}$ is an amide functional group, $R_c'$ is a triamine and $Hy_{c1}$ is a radical originating from a hydrophobic acid, $G_{c2}$ is a carbamate functional group and $Hy_{c2}$ is a radical originating from a hydrophobic alcohol.

In one embodiment, $F_c$ is an amide functional group, $G_{c1}$ is an ester functional group, $R_c'$ is a diacid amine and $Hy_{c1}$ is a radical originating from a hydrophobic alcohol, $G_{c2}$ is an amide functional group and $Hy_{c2}$ is a radical originating from a hydrophobic amine.

In one embodiment, $F_c$ is an amide functional group, $G_{c1}$ is an ester functional group, $R_c'$ is an alcohol acid amine and $Hy_{c1}$ is a radical originating from a hydrophobic acid, $G_{c2}$ is an amide functional group and $Hy_{c2}$ is a radical originating from a hydrophobic amine.

In one embodiment, $F_c$ is an amide functional group, $G_{c1}$ is an amide functional group, $R_c'$ is an alcohol diamine and $Hy_{c1}$ is a radical originating from a hydrophobic acid, $G_{c2}$ is a carbamate functional group and $Hy_{c2}$ is a radical originating from a hydrophobic amine.

In one embodiment, $F_c$ is an amide functional group, $G_{c1}$ is an ester functional group, $R_c'$ is a dialcohol amine and $Hy_{c1}$ is a radical originating from a hydrophobic acid, $G_{c2}$ is a carbamate functional group and $Hy_{c2}$ is a radical originating from a hydrophobic amine.

In one embodiment, $F_c$ is an amide functional group, $G_{c1}$ is an ester functional group, $R_c'$ is an acid alcohol amine and $Hy_{c1}$ is a radical originating from a hydrophobic alcohol, $G_{c2}$ is a carbamate functional group and $Hy_{c2}$ is a radical originating from a hydrophobic amine.

In one embodiment, $F_h$ is a carbamate functional group, $G_{h1}$ is an ester functional group, $R_h'$ is a diamine acid and $Hy_{h1}$ is a radical originating from a hydrophobic alcohol, $G_{h2}$ is an amide functional group and $Hy_{h2}$ is a radical originating from a hydrophobic acid.

In one embodiment, $F_h$ is a carbamate functional group, $G_{h1}$ is an ester functional group, $R_h'$ is an alcohol diamine and $Hy_{h1}$ is a radical originating from a hydrophobic acid, $G_{h2}$ is a carbamate functional group and $Hy_{h2}$ is a radical originating from a hydrophobic alcohol.

In one embodiment, $F_h$ is a carbamate functional group, $G_{h1}$ is an amide functional group, $R_h'$ is a triamine and $Hy_{h1}$ is a radical originating from a hydrophobic acid, $G_{h2}$ is a carbamate functional group and $Hy_{h2}$ is a radical originating from a hydrophobic alcohol.

In one embodiment, $F_h$ is a carbamate functional group, $G_{h1}$ is an ester functional group, $R_h'$ is a diacid amine and $Hy_{h1}$ is a radical originating from a hydrophobic alcohol, $G_{h2}$ is an amide functional group and $Hy_{h2}$ is a radical originating from a hydrophobic amine.

In one embodiment, $F_h$ is a carbamate functional group, $G_{h1}$ is an ester functional group, $R_h'$ is an alcohol acid amine and $Hy_{h1}$ is a radical originating from a hydrophobic acid, $G_{h2}$ is an amide functional group and $Hy_{h2}$ is a radical originating from a hydrophobic amine.

In one embodiment, $F_h$ is a carbamate functional group, $G_{h1}$ is an amide functional group, $R_h'$ is an alcohol diamine and $Hy_{h1}$ is a radical originating from a hydrophobic acid, $G_{h2}$ is a carbamate functional group and $Hy_{h2}$ is a radical originating from a hydrophobic amine.

In one embodiment, $F_h$ is a carbamate functional group, $G_{h1}$ is an ester functional group, $R_h'$ is a dialcohol amine and $Hy_{h1}$ is a radical originating from a hydrophobic acid, $G_{h2}$ is a carbamate functional group and $Hy_{h2}$ is a radical originating from a hydrophobic amine.

In one embodiment, $F_h$ is a carbamate functional group, $G_{h1}$ is an ester functional group, $R_h'$ is an acid alcohol amine and $Hy_{h1}$ is a radical originating from a hydrophobic alcohol, $G_{h2}$ is a carbamate functional group and $Hy_{h2}$ is a radical originating from a hydrophobic amine.

The polysaccharide can have a degree of polymerization m of between 5 and 10 000.

In one embodiment, it has a degree of polymerization m of between 10 and 1000.

In another embodiment, it has a degree of polymerization m of between 10 and 500.

The invention also relates to the synthesis of the polysaccharides according to the invention.

The invention also relates to the synthesis of the polysaccharides comprising carboxyls, at least one of which is functionalized by at least two hydrophobic groups, denoted $Hy_{c1}$ and $Hy_{c2}$ and/or $Hy_{h1}$ and $Hy_{h2}$, which are identical or different.

When the polysaccharides are chosen from the polysaccharides of general formulae II, III and IV, said synthesis comprises a stage of producing an amine intermediate $[Hy_c$-$G_c]_{rc}$-$R_c$—$NH_2$ or an ammonium salt $[Hy_c$-$G_c]_{rc}$-$R_c$—$NH_3^+$, the counterion of which is an anion chosen from halides, sulfates, sulfonates or carboxylates, and a stage of grafting this amine intermediate to a carboxyl functional group of a polysaccharide, $R_c$, $G_c$, $Hy_c$ and $r_c$ corresponding to the definitions given above.

In one embodiment, a stage of conversion of the hydroxyls of the polysaccharide to at least 15 carboxyl functional groups per 100 saccharide units is carried out by grafting compounds of formula Q-L' to at least 15 hydroxyl functional groups per 100 saccharide units of the polysaccharide, Q-L' being a precursor of the Q-L sequence, Q and L corresponding to the definitions given above.

In a preferred embodiment, the amine intermediate of formula $[Hy_c$-$G_c]_{rc}$-$R_c$—$NH_2$ or $[Hy_c$-$G_c]_{rc}$-$R_c$—$NH_3^+$ is obtained by reaction of a compound of formula $[G']_{rc}$-$R_c$—$NH_2$, G' being a carboxylic acid, amine or alcohol functional group, with the reactive functional group of the hydrophobic compound, $R_c$, $G_c$, $Hy_c$ and $r_c$ corresponding to the definitions given above.

Other methods of synthesis, such as those employing carbodiimides, well known to a person skilled in the art can also be used.

If necessary, in this stage of producing the amine intermediate, use is made of the protection and deprotection techniques well known to a person skilled in the art.

Preferably, the stage of grafting the amine intermediate to a carboxyl of the polysaccharide is carried out in an organic medium.

When the polysaccharides are chosen from the polysaccharides of general formulae V, VI or VII, said synthesis comprises a stage of producing an amine intermediate $[Hy_h$-$G_h]_{rh}$-$R_h$—$NH_2$ or an ammonium salt $[Hy_h$-$G_h]_{rh}$-$R_h$—$NH_3^+$, the counterion of which is an anion chosen from halides, sulfates, sulfonates or carboxylates, and a stage of grafting this amine intermediate to a hydroxyl of a polysaccharide, $R_h$, $G_h$, $Hy_h$ and $r_h$ corresponding to the definitions given above.

In one embodiment, a stage of conversion of the hydroxyls of the polysaccharide to at least 15 carboxyls per 100 saccharide units is carried out by grafting compounds of formula Q-L' to at least 15 hydroxyls per 100 saccharide units of the polysaccharide, Q-L' being a precursor of the Q-L sequence, Q and L corresponding to the definitions given above.

In a preferred embodiment, the amine intermediate of formula $[Hy_h$-$G_h]_{rh}$-$R_h$—$NH_2$ or $[Hy_h$-$G_h]_{rh}$-$R_h$—$NH_3^+$ is obtained by reaction of a compound of formula $[G_h']_{rh}$-$R_h$—$NH_2$, $G_h'$ being a carboxylic acid, amine or alcohol functional group, with the reactive functional group of the hydrophobic compound, $R_h$, $G_h$, $Hy_h$ and $r_h$ corresponding to the definitions given above.

Other methods of synthesis, such as those employing carbodiimides, well known to a person skilled in the art can also be used.

If necessary, in this stage of producing the amine intermediate, use is made of the protection and deprotection techniques well known to a person skilled in the art.

Preferably, the stage of grafting the amine intermediate to a carboxyl of the polysaccharide is carried out in an organic medium.

In one embodiment, the invention relates to a polysaccharide chosen from the group consisting of the following polysaccharides:

sodium dextranmethylcarboxylate modified by dihexyl aspartate sodium dextranmethylcarboxylate modified by dibenzyl aspartate sodium dextranmethylcarboxylate modified by dilauryl aspartate (dextran 10 kDa)

sodium dextranmethylcarboxylate modified by 3-amino-1, 2-propanediol dilaurate ester sodium dextranmethylcarboxylate modified by dioctyl aspartate sodium dextranmethylcarboxylate modified by dilauryl aspartate (dextran 5 kDa)

sodium dextranmethylcarboxylate modified by 2-[(2-dodecanoylamino-6-(dodecanoylamino)hexanoyl) amino]ethanamine sodium dextransuccinate modified by dioctyl aspartate sodium dextranmethylcarboxylate modified by 2,2',2"-(amino-bis[methyl phenylacetate])ethyl phenylacetate sodium dextranmethylcarboxylate modified by benzyl 2-amino-3-(octanoyloxy)propanoate N-(sodium methylcarboxylate) dextran carbamate modified by dioctyl aspartate dextran modified by N-(sodium methylcarboxylate) carbamate and dihexyl aspartate carbamate sodium dextranmethylcarboxylate modified by glutamic acid dilauryl amide sodium dextranmethylcarboxylate modified by diethyl-2-dodecanamide) aspartamide

EXAMPLE 1

Sodium dextranmethylcarboxylate Modified by dihexyl aspartate

Polymer 1

16 g (i.e. 296 mmol of hydroxyls) of dextran with a weight-average molar mass of approximately 40 kg/mol (Pharmacosmos) are dissolved in water at 42 g/l. 30 ml of 10N NaOH (296 mmol of NaOH) are added to this solution. The mixture is brought to 35° C. and then 46 g (396 mmol) of sodium chloroacetate are added. The temperature of the reaction medium is brought to 60° C. at 0.5° C./min and is then maintained at 60° C. for 100 minutes. The reaction medium is diluted with 200 ml of water, neutralized with acetic acid and purified by ultrafiltration through a 5 kD PES membrane against 6 volumes of water. The final solution is quantitatively determined by dry extract, in order to determine the concentration of polymer, and then quantitatively determined by acid/base titration in 50/50 (v/v) water/acetone, in order to determine the degree of conversion to methylcarboxylates.

According to the dry extract: [polymer]=31.5 mg/g

According to the acid/base titration: the degree of conversion of the hydroxyls to methylcarboxylates is 1.07 per saccharide unit.

The sodium dextranmethylcarboxylate solution is passed over a Purolite resin (anionic) in order to obtain the dextranmethylcarboxylic acid, which is subsequently lyophilized for 18 hours.

Dihexyl aspartate, para-toluenesulfonic acid salt, is obtained according to the process described in the patent (Kenji, M et al., U.S. Pat. No. 4,826,818).

10 g of dextranmethylcarboxylic acid (47.76 mmol of methylcarboxylic acid) are dissolved in DMF at 60 g/l and then cooled to 0° C. 2.0 g of dihexyl aspartate, para-toluenesulfonic acid salt (4.46 mmol) suspended in DMF at 100 g/l. 0.45 g of triethylamine (4.46 mmol) is subsequently added to this suspension. Once the polymer solution is at 0° C., a solution of NMM (1.35 g, 13.39 mmol) in DMF (530 g/l) and 1.45 g (13.39 mmol) of EtOCOCl are subsequently added. After reacting for 10 minutes, the dihexyl aspartate solution is added. The medium is subsequently maintained at 10° C. for 45 minutes. The medium is subsequently heated to 30° C. An imidazole solution (3.04 g in 9 ml of water) and 52 ml of water are added to the reaction medium. The polymer solution is ultrafiltered through a 10 kD PES membrane against 15 volumes of 0.9% NaCl solution and 5 volumes of water. The concentration of the polymer solution is determined by dry extract. A fraction of solution is lyophilized and analyzed by $^1$H NMR in $D_2O$ in order to determine the level of carboxyls converted to dihexyl aspartate amide.

According to the dry extract: [polymer 1]=31.1 mg/g

According to the $^1$H NMR: the degree of functionalization of the acids by the dihexyl aspartate per saccharide unit is 0.075.

EXAMPLE 2

Sodium dextranmethylcarboxylate Modified by dibenzyl aspartate

Polymer 2

Dibenzyl aspartate, para-toluenesulfonic acid salt, is obtained according to the process described in the patent (Kenji, M et al., U.S. Pat. No. 4,826,818).

A sodium dextranmethylcarboxylate modified by dibenzyl aspartate is obtained by a process similar to that described in example 1.

According to the dry extract: [polymer 2]=35 mg/g

According to the $^1$H NMR: the degree of functionalization of the acids by dibenzyl aspartate is 0.085.

EXAMPLE 3

Sodium dextranmethylcarboxylate Modified by dilauryl aspartate (Dextran 10 kDa)

Polymer 3

Dilauryl aspartate, para-toluenesulfonic acid salt, is obtained according to the process described in the patent (Kenji, M et al., U.S. Pat. No. 4,826,818).

A sodium dextranmethylcarboxylate, synthesized according to the process described in example 1 using a dextran with a weight-average molecular weight of approximately 10 kg/mol (Pharmacosmos), modified by dilauryl aspartate is obtained by a process similar to that described in example 1.

According to the dry extract: [polymer 3]=17.8 mg/g

According to the $^1$H NMR: the degree of functionalization of the acids by dilauryl aspartate is 0.05.

EXAMPLE 4

Sodium dextranmethylcarboxylate Modified by 3-amino-1,2-propanediol dilaurate ester Polymer 4

3-Amino-1,2-propanediol dilaurate ester, para-toluenesulfonic acid salt, is obtained according to the process described in the patent (Kenji, M et al., U.S. Pat. No. 4,826,818).

A sodium dextranmethylcarboxylate modified by 3-amino-1,2-propanediol dilaurate ester is obtained by a process similar to that described in example 1.

According to the dry extract: [polymer 4]=18.5 mg/g

According to the $^1$H NMR: the degree of functionalization of the acids by 3-amino-1,2-propanediol dilaurate ester per saccharide unit is 0.045.

EXAMPLE 5

Sodium dextranmethylcarboxylate Modified by dioctyl aspartate

Polymer 5

Dioctyl aspartate, para-toluenesulfonic acid salt, is obtained according to the process described in the patent (Kenji, M et al., U.S. Pat. No. 4,826,818).

A sodium dextranmethylcarboxylate, synthesized according to the process described in example 1 using a dextran with a weight-average molecular weight of approximately 10 kg/mol (Pharmacosmos), modified by dioctyl aspartate is obtained by a process similar to that described in example 1.

According to the dry extract: [polymer 5]=22.2 mg/g

According to the $^1$H NMR: the degree of functionalization of the acids by dioctyl aspartate is 0.05.

EXAMPLE 6

Sodium dextranmethylcarboxylate Modified by dilauryl aspartate (Dextran 5 kDa)

Polymer 6

Dilauryl aspartate, para-toluenesulfonic acid salt, is obtained according to the process described in the patent (Kenji, M et al., U.S. Pat. No. 4,826,818).

A sodium dextranmethylcarboxylate, synthesized according to the process described in example 1 using a dextran with a weight-average molecular weight of approximately 5 kg/mol (Pharmacosmos), modified by dilauryl aspartate is obtained by a process similar to that described in example 1.

According to the dry extract: [polymer 6]=8.9 mg/g

According to the $^1$H NMR: the degree of functionalization of the acids by dilauryl aspartate is 0.05.

EXAMPLE 7

Sodium dextranmethylcarboxylate Modified by 2-[(2-dodecanoylamino-6-(dodecanoylamino)hexanoyl)amino]ethanamine Polymer 7

N,N'-Bis(dodecanoyl)lysine is obtained from the ethyl ester of L-lysine, hydrochloric acid salt, (Bachem) and dodecanoic acid (Sigma) according to the process described in the publication (Pal, A et al., Tetrahedron, 2007, 63, 7334-7348).

2-[(2-Dodecanoylamino-6-(dodecanoylamino)hexanoyl) amino]ethanamine, hydrochloric acid salt, is obtained from N,N'-bis(dodecanoyl)lysine and ethylenediamine (Roth) according to the processes described in the publications (Paul, R et al., J. Org. Chem., 1962, 27, 2094-2099, and Dale, D. J. et al., Org. Process. Res. Dev., 2002, 6, 767-772).

A sodium dextranmethylcarboxylate, synthesized according to the process described in example 1 using a dextran with a weight-average molecular weight of approximately 10 kg/mol (Pharmacosmos), modified by 2-[(2-dodecanoylamino-6-(dodecanoylamino)hexanoyl)amino]ethanamine is obtained by a process similar to that described in example 1.

According to the dry extract: [polymer 7]=16.9 mg/g

According to the $^1$H NMR: the degree of functionalization of the acids by 2-[(2-dodecanoylamino-6-(dodecanoylamino)hexanoyl)amino]ethanamine is 0.02.

EXAMPLE 8

Sodium dextransuccinate Modified by dioctyl aspartate

Polymer 8

Dioctyl aspartate, para-toluenesulfonic acid salt, is obtained according to the process described in the patent (Kenji, M et al., U.S. Pat. No. 4,826,818).

Sodium dextransuccinate is obtained from dextran 10 (Pharmacosmos) according to the method described in the paper by Sanchez-Chaves et al. (Sanchez-Chaves, Manuel et al., Polymer, 1998, 39 (13), 2751-2757). The level of carboxyls per glycoside unit is 1.41, according to the $^1$H NMR in D$_2$O/NaOD.

A sodium dextransuccinate modified by dioctyl aspartate is obtained by a process similar to that described in example 1.

According to the dry extract: [polymer 8]=19.3 mg/g

According to the $^1$H NMR: the degree of functionalization of the acids by dioctyl aspartate per saccharide unit is 0.05.

EXAMPLE 9

Sodium dextranmethylcarboxylate Modified by 2,2',2"-(amino-bis[methyl phenylacetate])ethyl phenylacetate Polymer 9

2,2',2"-(Amino-bis[methyl phenylacetate])ethyl phenylacetate, para-toluenesulfonic acid salt, is obtained from 2-amino-2-(hydroxymethyl)-1,3-propanediol (Tris) (Aldrich) and phenylacetic acid (Aldrich) according to the process described in the patent (Kenji, M et al., U.S. Pat. No. 4,826,818).

A sodium dextranmethylcarboxylate, synthesized according to the process described in example 1 using a dextran with a weight-average molecular weight of approximately 10 kg/mol (Pharmacosmos), modified by 2,2',2"-(amino-bis [methyl phenylacetate])ethyl phenylacetate is obtained by a process similar to that described in example 1.

According to the dry extract: [polymer 9]=15.4 mg/g

According to the $^1$H NMR: the degree of functionalization of the acids by 2,2',2"-(amino-bis[methyl phenylacetate]) ethyl phenylacetate is 0.04.

EXAMPLE 10

Sodium dextranmethylcarboxylate Modified by benzyl 2-amino-3-(octanoyloxy)propanoate Polymer 10

Benzyl 2-amino-3-(octanoyloxy)propanoate, para-toluenesulfonic acid salt, is obtained from L-serine benzyl ester, hydrochloric acid salt, and octanoic acid according to the process described in the patent (Kenji, M et al., U.S. Pat. No. 4,826,818).

Using a dextran with a weight-average molecular weight of approximately 10 kg/mol (Pharmacosmos), modified by benzyl 2-amino-3-(octanoyloxy)propanoate is obtained by a process similar to that described in example 1.

According to the dry extract: [polymer 10]=21.2 mg/g

According to the $^1$H NMR: the degree of functionalization of the acids by benzyl 2-amino-3-(octanoyloxy)propanoate per saccharide unit is 0.045.

EXAMPLE 11

N-(Sodium methylcarboxylate)dextran carbamate Modified by dioctyl aspartate

Polymer 11

Dioctyl aspartate, para-toluenesulfonic acid salt, is obtained according to the process described in the patent (Kenji, M et al., U.S. Pat. No. 4,826,818).

11.5 g (i.e., 0.21 mol of hydroxyl) of dextran with a weight-average molar mass of approximately 10 kg/mol (Bachem) are dissolved in a DMF/DMSO mixture. The mixture is brought to 130° C. with stirring and 13.75 g (0.11 mol) of ethyl isocyanatoacetate are gradually introduced. After reacting for 1 h, the medium is diluted in water and purified by diafiltration through a 5 kD PES membrane against 0.1N NaOH, 0.9% NaCl and water. The final solution is quantitatively determined by dry extract, in order to determine the concentration of polymer, and then quantitatively determined by acid/base titration in 50/50 (v/v) water/acetone, in order to determine the degree of conversion of the hydroxyls to N-methylcarboxylate carbamates.

According to the dry extract: [polymer]=38.9 mg/g

According to the acid/base titration: the degree of conversion of the hydroxyls to N-methylcarboxylate carbamate functional groups is 1.08 per saccharide unit.

The solution of N-(sodium methylcarboxylate) dextran carbamate is passed over a Purolite resin (anionic) in order to obtain the N-(methylcarboxylic acid) dextran carbamate, which is subsequently lyophilized for 18 hours.

5 g of N-(methylcarboxylic acid) dextran carbamate (20 mmol of N-(methylcarboxylic acid)) are dissolved in DMF at 50 g/l and then cooled to 0° C. 0.95 g of dioctyl aspartate, para-toluenesulfonic acid salt, (0.18 mmol) is suspended in DMF at 100 g/l. 0.02 g of triethylamine (0.18 mmol) is subsequently added to this suspension. 2.22 g (22 mmol) of NMM and 2.38 g (22 mmol) of EtOCOCl are subsequently added. After reacting for 10 minutes, the dioctyl aspartate suspension is added. The medium is subsequently maintained at 10° C. for 45 minutes. The medium is subsequently heated to 50° C. A 600 g/l aqueous imidazole solution and 25 ml of water are added at 30° C. After stirring at 50° C. for 1 h 30, the solution obtained is ultrafiltered through a 10 kD PES membrane against 0.1N NaOH, 0.9% NaCl and water. The concentration of the polymer solution is determined by dry extract. A fraction of solution is lyophilized and analyzed by $^1$H NMR in $D_2O$ in order to determine the level of carboxyls converted to dioctyl aspartate amide.

According to the dry extract: [polymer 11]=21.2 mg/g
According to the $^1$H NMR: the degree of functionalization of the acids by dioctyl aspartate per saccharide unit is 0.09.

EXAMPLE 12

Dextran Modified by N-(sodium methylcarboxylate)carbamate and dihexyl aspartate carbamate Polymer 12
Dihexyl aspartate, para-toluenesulfonic acid salt, is obtained according to the process described in the patent (Kenji, M et al., U.S. Pat. No. 4,826,818).

Dihexyl 2-isocyanatobutanedioate is obtained from dihexyl aspartate according to the process described in the publication (Knockler, H.-J. et al., Synlett, 1997, 925-928).

2.7 g (i.e., 50 mmol of hydroxyls) of dextran with a weight-average molar mass of approximately 10 kg/mol (Bachem) are dissolved in a DMF/DMSO mixture. The mixture is brought to 130° C. with stirring and 3.2 g (25 mmol) of ethyl isocyanatoacetate and then 3.9 g (8 mmol) of dihexyl 2-isocyanatobutanedioate are gradually introduced. After reacting for 1 h, the medium is diluted in water and purified by diafiltration through a 5 kD PES membrane against 0.1N NaOH, 0.9% NaCl and water. The final solution is quantitatively determined by dry extract, in order to determine the concentration of polymer. A fraction of solution is lyophilized and analyzed by $^1$H NMR in $D_2O$ in order to determine the degree of conversion of the hydroxyls to N-(sodium methylcarboxylate) carbamate and the degree of the functionalization of the hydroxyls to give dihexyl aspartate carbamate.

According to the dry extract: [polymer 12]=8.2 mg/g
According to the $^1$H NMR: the degree of conversion of the hydroxyls to N-(sodium methylcarboxylate) carbamate is 1.1 and the degree of functionalization of the hydroxyls to give dihexyl aspartate carbamate is 0.05.

EXAMPLE 13

Sodium dextranmethylcarboxylate Modified by dilauryl aspartate (Dextran 5 kDa)

Polymer 13
Dilauryl aspartate, para-toluenesulfonic acid salt, is obtained according to the process described in the patent (Kenji, M et al., U.S. Pat. No. 4,826,818).

On twice repeating the process for the methylcarboxylation of dextran described in example 1 using a dextran with a weight-average molecular weight of approximately 5 kg/mol (Pharmacosmos), a sodium dextranmethylcarboxylate with a degree of conversion of the hydroxyls to methylcarboxylates of 1.66 per saccharide unit is obtained. A sodium dextranmethylcarboxylate modified by dilauryl aspartate is obtained from this sodium dextranmethylcarboxylate by a process similar to that described in example 1.

According to the dry extract: [polymer 13]=10.1 mg/g
According to the $^1$H NMR: the degree of functionalization of the acids by dilauryl aspartate is 0.05.

EXAMPLE 14

Sodium dextranmethylcarboxylate Modified by Glutamic Acid dilauryl amide

Polymer 14
L-Glutamic acid dilauryl amide, the α-amine of which is protected by a Fmoc, is obtained from Fmoc-L-glutamic acid (Bachem) and dodecylamine according to the process described in the publication (Pal, A et al., Tetrahedron, 2007, 63, 7334-7348). The Fmoc group is subsequently removed by treatment in a piperidine solution in order to obtain the glutamic acid dilauryl amide.

A sodium dextranmethylcarboxylate, synthesized according to the process described in example 1 using a dextran with a weight-average molecular weight of approximately 10 kg/mol (Pharmacosmos), modified by glutamic acid dilauryl amide is obtained by a process similar to that described in example 1.

According to the dry extract: [polymer 14]=15.6 mg/g
According to the $^1$H NMR: the degree of functionalization of the acids by glutamic acid dilauryl amide is 0.07.

EXAMPLE 15

Sodium dextranmethylcarboxylate Modified by di(ethyl-2-dodecanamide)aspartamide

Polymer 15
N-(2-Aminoethyl)dodecanamide is obtained from the methyl ester of dodecanoic acid (Sigma) and ethylenediamine (Roth) according to the process described in the patent (Weiner, N. et al., U.S. Pat. No. 2,387,201).

Diethyl-2-dodecanamide) L-aspartamide, the α-amine of which is protected by a Fmoc, is obtained from Fmoc-L-aspartic acid (Bachem) and N-(2-aminoethyl)dodecanamide according to the process described in the publication (Pal, A et al., Tetrahedron, 2007, 63, 7334-7348). The Fmoc group is subsequently removed by treatment in a piperidine solution in order to obtain diethyl-2-dodecanamide) aspartamide.

A sodium dextranmethylcarboxylate, synthesized according to the process described in example 1 using a dextran with a weight-average molecular weight of approximately 5 kg/mol (Pharmacosmos), modified by di(ethyl-2-dodecanamide) aspartamide is obtained by a process similar to that described in example 1.

According to the dry extract: [polymer 15]=9.2 mg/g
According to the $^1$H NMR: the degree of functionalization of the acids by di(ethyl-2-dodecanamide) aspartamide is 0.05.

The invention also relates to the use of the functionalized polysaccharides according to the invention in the preparation of pharmaceutical compositions.

The invention also relates to a pharmaceutical composition comprising one of the polysaccharides according to the invention as described above and at least one active principle.

The invention also relates to a pharmaceutical composition according to the invention as described above, wherein the active principle is chosen from the group consisting of proteins, glycoproteins, peptides and nonpeptide therapeutic molecules.

The term "active principle" is understood to mean a product in the form of a single chemical entity or in the form of a combination having a physiological activity. Said active principle can be exogenous, that is to say that it is introduced by the composition according to the invention. It can also be endogenous, for example the growth factors which will be secreted in a wound during the first stage of healing and which can be retained on said wound by the composition according to the invention.

Depending on the pathologies targeted, it is intended for a local or systemic treatment.

In the case of local and systemic releases, the methods of administration envisaged are by the intravenous, subcutaneous, intradermal, transdermal, intramuscular, oral, nasal, vaginal, ocular, buccal or pulmonary routes, and the like.

The pharmaceutical compositions according to the invention are either in the liquid form, in aqueous solution, or in the powder, implant or film form. They additionally comprise the conventional pharmaceutical excipients well known to a person skilled in the art.

Depending on the pathologies and methods of administration, the pharmaceutical compositions can advantageously comprise, in addition, excipients which make it possible to formulate them in the form of a gel, sponge, injectable solution, solution to be taken orally, lyophilized tablet, and the like.

The invention also relates to a pharmaceutical composition according to the invention as described above, which can be administered in the form of a stent, of a film or coating of implantable biomaterials, or of an implant.

What is claimed is:

1. An anionic polysaccharide, of formula II, from dextrans comprising carboxyl groups, the dextrans comprising carboxyl groups being obtained from neutral dextrans, hydroxyl groups of which have been converted to carboxyl groups, and at least one of the carboxyl groups of the dextrans is substituted by at least two hydrophobic radicals, each denoted $-Hy_c$, which are identical or different, and wherein any of the carboxyl groups of the dextrans that are substituted are substituted only by the at least two hydrophobic radicals:

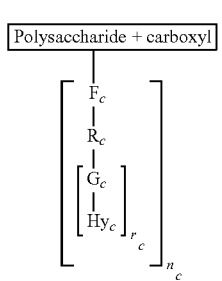

Formula II wherein:
the polysaccharide is dextran,
the degree of conversion of the hydroxyl groups to carboxyl groups per saccharide unit of the dextrans is equal to or greater than 0.15,
$n_c$ represents the degree of functionalization of the saccharide units of the dextrans by $-F_c-R_c-[G_c-Hy_c]_{rc}$ and $n_c$ is from 0.01 to 0.5, $F_c$ is either an amide functional group or an ester functional group,
the carboxyl groups of the dextrans that are not substituted by the at least two hydrophobic radicals are in the form of a salt of carboxylate with a cation,
$G_c$ is an amide functional group, an ester functional group or a carbamate functional group resulting from the coupling between a reactive functional group of a hydrophobic compound ($Hy_c'$) and a reactive functional group of $R_c'$, a precursor of connecting arm $R_c$,
$Hy_c$ are radicals, which are identical or different, resulting from the coupling between a reactive functional group of a hydrophobic compound ($Hy_c'$) and a reactive functional group of $R_c'$, a precursor of connecting arm $R_c$, the radicals being chosen from (1) a radical originating from a hydrophobic alcohol resulting from the coupling, wherein the hydrophobic alcohol is chosen from alcohols composed of a saturated or unsaturated and branched or unbranched alkyl chain comprising from 4 to 18 carbons, (2) a radical originating from a hydrophobic acid resulting from the coupling, wherein the hydrophobic acid is selected from the group consisting of acids composed of a saturated or unsaturated and branched or unbranched alkyl chain comprising from 6 to 50 carbons, or (3) a radical originating from a hydrophobic amine resulting from the coupling, wherein the hydrophobic amine is selected from the group consisting of amines composed of a saturated or unsaturated and linear or branched alkyl chain comprising from 6 to 18 carbons,
$R_c$, the connecting arm, is an at least trivalent radical chosen from a radical composed of a chain comprising from 1 to 15 carbons, a radical composed of a chain comprising 1 to 15 carbons which is branched and/or unsaturated, a radical composed of a chain comprising 1 to 15 carbons which comprises one or more heteroatoms, and a radical composed of a chain comprising 1 to 15 carbons which comprises one or more saturated, unsaturated or aromatic rings or heterocycles, the radical $R_c$ resulting from the reaction of a precursor $R_c'$ having at least three reactive functional groups, which are identical or different, chosen from the group consisting of alcohol, acid and amine functional groups, and
$r_c$ is an integer representing the number of hydrophobic groups grafted to the connecting arm $R_c$, wherein $r_c$ is an integer of 2 or more.

2. The polysaccharide as claimed in claim 1, which is chosen from the group of the polysaccharides of formula III:

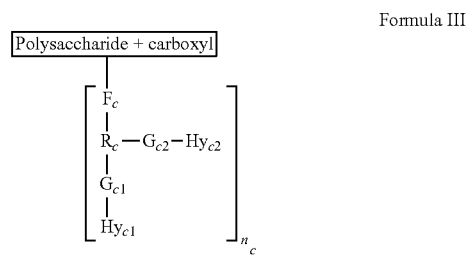

Formula III wherein:
the polysaccharide is dextran,
$n_c$ represents the degree of functionalization of the saccharide units of the dextrans by $-F_c-R_c-[G_c-Hy_c]_{rc}$ and $n_c$ is between 0.01 and 0.5, $F_c$ is either an amide functional group or an ester functional group, $R_c$, the connecting arm, is an at least trivalent radical chosen from a radical composed of a chain comprising from 1 to 15 carbons, a radical composed of a chain comprising 1 to 15 carbons which is branched and/or unsaturated, a radical composed of a chain comprising 1 to 15 carbons which comprises one or more heteroatoms, and a radical composed of a chain comprising 1 to 15 carbons which comprises one or more saturated, unsaturated or aromatic rings or heterocycles, the radical $R_c$ resulting from the reaction of a precursor $R_c'$ having at least three reactive functional groups, which are identical or different, chosen from the group consisting of alcohol, acid and amine functional groups, $G_{c1}$ and $G_{c2}$, which are identical or different, correspond to the definition of $G_c$, $Hy_{c1}$ and $Hy_{c2}$, which are identical or different, correspond to the definition of $Hy_c$.

3. The polysaccharide as claimed in claim 1, wherein the dextrans, before at least one of the carboxyl groups is substituted by at least two hydrophobic radicals, is of general formula VIII:

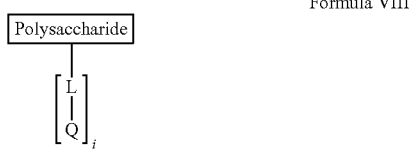

Formula VIII wherein:
the polysaccharide is dextran and L is a bond resulting from the coupling between a precursor of a connecting arm Q and an —OH functional group of the dextran and is an ester, carbamate or ether functional group,
i represents the degree of conversion of the hydroxyl groups to L-Q sequences per saccharide unit of the polysaccharide, and
Q is a connecting arm comprising from 1 to 18 carbons that is optionally branched and/or unsubstituted, that comprises one or more heteroatoms, and that comprises at least one carboxyl functional group —$CO_2H$.

4. The polysaccharide as claimed in claim 3, wherein the L-Q sequence is

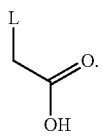

5. The polysaccharide as claimed in claim 3, wherein the L-Q sequence is

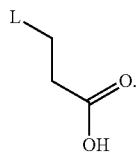

6. The polysaccharide as claimed in claim 1, wherein the -$Hy_c$ radical is a radical originating from a hydrophobic alcohol resulting from the coupling between the hydroxyl functional group of the hydrophobic alcohol and at least one reactive functional group carried by the precursor $R_c'$ of the at least trivalent radical $R_c$, and
$G_c$ is either an ester functional group or a carbamate functional group.

7. The polysaccharide as claimed in claim 6, wherein the hydrophobic alcohol is chosen from alcohols composed of a saturated or unsaturated and branched or unbranched alkyl chain comprising from 4 to 18 carbons.

8. The polysaccharide as claimed in claim 6, wherein the hydrophobic alcohol is chosen from alcohols composed of a saturated or unsaturated and branched or unbranched alkyl chain comprising more than 18 carbons.

9. The polysaccharide as claimed in claim 1, wherein the -$Hy_c$ radical is a radical originating from a hydrophobic acid resulting from the coupling between the carboxyl functional group of the hydrophobic acid and at least one reactive functional group carried by the precursor $R_c'$ of the at least trivalent radical $R_c$, and
$G_c$ is either an ester functional group or an amide functional group.

10. The polysaccharide as claimed in claim 9, wherein the hydrophobic acid is chosen from the group consisting of fatty acids composed of a saturated or unsaturated and branched or unbranched alkyl chain comprising from 6 to 50 carbons.

11. The polysaccharide as claimed in claim 1, wherein the -$Hy_c$ radical is a radical originating from a hydrophobic amine resulting from the coupling between the amine functional group of the hydrophobic amine and at least one reactive functional group carried by the precursor $R_c'$ of the at least trivalent radical $R_c$, and
$G_c$ is either an amide functional group or a carbamate functional group.

12. The polysaccharide as claimed in claim 11, wherein the hydrophobic amine is chosen from the group consisting of fatty amines.

13. The polysaccharide as claimed in claim 11, wherein the hydrophobic amine is chosen from the group consisting of amines composed of a saturated or unsaturated and linear or branched alkyl chain comprising from 6 to 18 carbons.

14. The polysaccharide as claimed in claim 1, wherein the at least trivalent precursor $R_c'$ is chosen from amino acids carrying two acid functional groups.

15. The polysaccharide as claimed in claim 1, wherein the at least trivalent precursor $R_c'$ is chosen from amino acids carrying two amine functional groups.

16. The polysaccharide as claimed in claim 1, wherein the at least trivalent precursor $R_c'$ is chosen from amino acids carrying an alcohol functional group.

17. The polysaccharide as claimed in claim 1, wherein the at least trivalent precursor $R_c'$ is chosen from alcohol amines.

18. The polysaccharide as claimed in claim 1, wherein the at least trivalent precursor $R_c'$ is chosen from triamines.

19. The polysaccharide as claimed in claim 1, wherein the at least trivalent precursor $R_c'$ is chosen from diacid alcohols.

20. A pharmaceutical composition comprising the anionic polysaccharide as claimed in claim 1 and at least one active principle.

21. The pharmaceutical composition as claimed in claim 20, which can be administered by the oral, nasal, vaginal or buccal route.

22. The pharmaceutical composition as claimed in claim 20, wherein the active principle is chosen from the group consisting of proteins, glycoproteins, peptides and nonpeptide therapeutic molecules.

\* \* \* \* \*

UNITED STATES PATENT AND TRADEMARK OFFICE
CERTIFICATE OF CORRECTION

| | | |
|---|---|---|
| PATENT NO. | : 9,115,218 B2 | Page 1 of 1 |
| APPLICATION NO. | : 13/024100 | |
| DATED | : August 25, 2015 | |
| INVENTOR(S) | : Charvet et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 806 days.

Signed and Sealed this
Nineteenth Day of April, 2016

Michelle K. Lee
*Director of the United States Patent and Trademark Office*